United States Patent
Lee et al.

(10) Patent No.: US 8,216,826 B2
(45) Date of Patent: Jul. 10, 2012

(54) FLUID ANALYZING APPARATUS

(75) Inventors: Kun Feng Lee, Hunei Township (TW);
Pei-Shin Jiang, Taichung (TW);
Yuh-Jiuan Lin, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 914 days.

(21) Appl. No.: 12/251,274

(22) Filed: Oct. 14, 2008

(65) Prior Publication Data

US 2009/0041623 A1 Feb. 12, 2009

Related U.S. Application Data

(63) Continuation-in-part of application No. 10/674,403, filed on Oct. 1, 2003.

(30) Foreign Application Priority Data

Jan. 21, 2003 (TW) .............................. 92102221 A

(51) Int. Cl.
*C12M 1/34* (2006.01)
(52) U.S. Cl. ............... 435/286.5; 435/283.1; 435/287.1; 435/288.2; 427/211; 427/10; 436/149

(58) Field of Classification Search .................. None
See application file for complete search history.

(56) References Cited

U.S. PATENT DOCUMENTS

| | | | |
|---|---|---|---|
| 5,225,163 A * | 7/1993 | Andrews | 422/430 |
| 6,144,447 A | 11/2000 | Ohman et al. | |
| 6,306,659 B1 | 10/2001 | Parce et al. | |
| 6,398,765 B1 | 6/2002 | Hung | |
| 2002/0012616 A1* | 1/2002 | Zhou et al. | 422/130 |
| 2002/0028463 A1* | 3/2002 | Duffy | 435/6 |
| 2002/0176804 A1* | 11/2002 | Strand et al. | 422/100 |

\* cited by examiner

*Primary Examiner* — N. C. Yang

(74) *Attorney, Agent, or Firm* — Birch, Stewart, Kolasch & Birch, LLP

(57) ABSTRACT

A fluid analyzing apparatus. The fluid analyzing apparatus sequentially or simultaneously detects and analyzes a multiplex fluid sample with suitable analyzing elements. Meanwhile, the fluid analyzing apparatus may be disassembled to a first unit, a second unit and a third unit, such that the analyzing elements therein are easily disposed and replaced. The fluid analyzing apparatus analyzes and detects the multiplex fluid sample by allowing the multiplex fluid sample to sequentially or simultaneously flow through a plurality of target chambers. The fluid analyzing apparatus sequentially or simultaneously transports the multiplex fluid sample to the target chambers, thereby enhancing the speed and analysis thereof.

10 Claims, 9 Drawing Sheets

FLUID ANALYZING APPARATUS

CROSS REFERENCE TO RELATED APPLICATIONS

This application is a Continuation-In-Part of pending U.S. patent application Ser. No. 10/674,403, filed Oct. 1, 2003 and entitled "Fluid analyzing apparatus". This Application claims priority of Taiwan Patent Application No. 92101221, filed on Jan. 21, 2003, the entirety of which is incorporated by reference herein.

BACKGROUND OF THE INVENTION

1. Field of the Invention

The present invention relates to a fluid analyzing apparatus, and in particular to a fluid analyzing apparatus that sequentially or simultaneously analyzes a multiplex fluid sample.

2. Description of the Related Art

A multiplex fluid sample, such as blood and urine, may be composed of many constituents with unknown concentrations. The multiplex fluid sample may include substances of interest or prohibited substances. In order to analyze or sieve out specific constituents in the multiplex fluid sample, U.S. Pat. Nos. 6,398,765, 6,306,659 and 6,144,447 discloses several conventional fluid analyzing devices.

In the U.S. Pat. No. 6,398,765, the fluid analyzing device is a complex structural design. It is composed of many ducts for analyzing of breast milk.

In the U.S. Pat. No. 6,306,659, the fluid analyzing device belongs to one kind of microfluidic devices. The device with numerous working areas is used for analyzing a plurality of compounds and performing high throughput screening assays. Meanwhile, the micro-ducts in this fluid analyzing device are manufactured by means of a complex MEMS process. The fluid analyzing device does not disclose the function of sequentially or simultaneously analyzing the compounds.

In the U.S. Pat. No. 6,144,447, the fluid analyzing device employs electrochemical and optical means to measure different physical or chemical parameters of a multiplex fluid sample in a flow cell. The electrochemical and optical means are directly disposed on the wall of the flow cell of the fluid analyzing device, thereby limiting the size of the flow cell and the amount of the multiplex fluid sample flowing therein. Accordingly, since the multiplex fluid sample flows in the flow cell with a limited size, the friction and surface tension between the multiplex fluid sample and wall of the flow cell are greater. The flowing speed of the multiplex fluid sample near the wall of the flow cell is different from that near the center thereof. Thus, the analysis of the multiplex fluid sample is adversely affected.

Hence, there is a need to provide an improved fluid analyzing apparatus to overcome the aforementioned problems. The present fluid analyzing apparatus sequentially or simultaneously detects and analyzes a multiplex fluid sample with suitable analyzing elements. Furthermore, the fluid analyzing apparatus analyzes and detects the multiplex fluid sample by allowing the multiplex fluid sample to sequentially or simultaneously flow through a plurality of target chambers with a suitable volume, thereby enhancing the speed and analysis thereof.

SUMMARY OF THE INVENTION

Accordingly, the invention provides a fluid analyzing apparatus to sequentially analyze a multiplex fluid sample. The fluid analyzing apparatus comprises a first unit, a second unit, a third unit, upper analyzing elements and lower analyzing elements. The first unit has a fluid inlet, a fluid outlet and a first upper analyzing elements fixation portion. The first upper analyzing elements fixation portion is formed on the lower part of the first unit and corresponds to the first lower analyzing elements fixation portion of the second unit. The second unit is disposed under the first unit and has the fluid transmission pipeline, a first lower analyzing elements fixation portion, and a second upper analyzing elements fixation portion. The first lower analyzing elements fixation portion is formed on the upper part of the second unit and corresponds to the first upper analyzing elements fixation portion of the first unit. The second upper analyzing elements fixation portion is formed on the lower part of the second unit and corresponds to the second lower analyzing elements fixation portion of the third unit. The third unit is disposed under the second unit and has a second lower analyzing elements fixation portion. The second lower analyzing elements fixation portion is formed on the upper part of the third unit and corresponds to the second upper analyzing elements fixation portion of the second unit. Therefore, by the combination of a first unit, a second unit, a third unit, the target chambers are formed by assembly between the upper analyzing elements fixation portion, the lower analyzing elements fixation portion, and sensing elements. Meanwhile, the fluid transmission pipeline of the second unit is sequentially connected to the distal portion of fluid inlet wherein the first unit, target chambers wherein the second unit, and distal portion of fluid outlet wherein the first unit. Furthermore, the multiplex fluid sample is flows in of the fluid analyzing apparatus via the fluid inlet, flows through the fluid analyzing apparatus via the fluid transmission pipeline and target chambers, finally flows out of the fluid analyzing apparatus via the fluid outlet.

Accordingly, the fluid transmission pipeline of the second unit is sequentially connected to the distal portion of fluid inlet, target chambers, and distal portion of fluid outlet with an inclined angle (45 degrees).

Accordingly, the fluid analyzing apparatus further comprises a first sealing element disposed between the first upper analyzing elements fixation portion and first lower analyzing elements fixation portion to prevent leakage of the multiplex fluid sample from the upper target chambers.

Accordingly, the fluid analyzing apparatus further comprises a second sealing element disposed between the second upper analyzing elements fixation portion and second lower analyzing elements fixation portion to prevent leakage of the multiplex fluid sample from the lower target chambers.

Accordingly, the upper analyzing elements and the lower analyzing elements further comprise the signal connecting portion extending out of the fluid analyzing apparatus.

Accordingly, the first and second analyzing elements are physical or/and biological or/and chemical sensing elements. One embodiment of the first and second analyzing elements is quartz crystal microbalance (QCM).

Accordingly, the physical sensing element is an electrode, a QCM, a flexural plate wave (FPW) device, a thermal sensing element, a pressure sensing element, an optical sensing element or a viscosity sensing element. One embodiment of the first and second analyzing elements is QCM.

Accordingly, the biological sensing element is a nucleic acid, protein, antibody, enzyme, microorganism or other biochemical substances.

Accordingly, the fluid analyzing apparatus further comprises at least one bolt to combine the first, second and third units.

Accordingly, the first, second and third units are composed of acrylic, Teflon or glass.

Accordingly, the fluid analyzing apparatus further comprises a pump to pump the multiplex fluid sample into the fluid analyzing apparatus.

Accordingly, the multiplex fluid sample is respectively analyzed or detected by the first and second analyzing elements.

Accordingly, the fluid analyzing apparatus could easy to take apart for replacement of analyzing elements.

The invention provides a fluid analyzing apparatus to simultaneously analyze a multiplex fluid sample. The fluid analyzing apparatus comprises a first unit, a second unit, a third unit, and the analyzing elements. The first unit has a fluid inlet and a dispersing portion disposed on the lower part of the first unit and connected to the fluid inlet. The multiplex fluid sample flows into the dispersing portion via the fluid inlet. The second unit is disposed under the first unit and has the fluid pipelines, the upper analyzing elements fixation portion, and a collective portion. The upper analyzing elements fixation portion, and collective portion are formed on the lower past of the second unit. The third unit is disposed under the second unit and has the lower analyzing elements fixation portion, and a fluid outlet. The lower analyzing elements fixation portion is formed on the upper part of the third unit and corresponds to the upper analyzing elements fixation portion. The fluid outlet is connected to the collective portion of the second unit. The multiplex fluid sample flows out of the fluid analyzing apparatus via the fluid outlet. Therefore, by combination of a first unit, a second unit, and a third unit, the target chambers are formed by assembly between the upper analyzing elements fixation portion, the lower analyzing elements fixation portion, and sensing elements. Meanwhile, the fluid pipeline of the second unit is sequentially connected to the dispersing portion of the first unit, target chamber of the second unit, and the collective portion of the second unit. Furthermore, the multiplex fluid sample flows in of the fluid analyzing apparatus via the fluid inlet, flow through the fluid analyzing apparatus via the dispersing portion, the fluid pipeline, the target chambers, and the collective portion, finally flows out of the fluid analyzing apparatus via the fluid outlet.

Accordingly, the pipeline of the second unit is connected to the dispersing portion of the first unit, the target chamber of the second unit, and the collective portion of the second unit with an inclined angle.

Accordingly, the fluid analyzing apparatus further comprises a sealing element disposed between the upper analyzing elements fixation portion and lower analyzing elements fixation portion to prevent leakage of the multiplex fluid sample from the target chamber.

Accordingly, the analyzing elements further comprise a signal connecting portion extending out of the fluid analyzing apparatus.

Accordingly, the analyzing elements are physical or/and biological or/and chemical sensing elements. One embodiment of the first and second analyzing elements is quartz crystal microbalance (QCM).

Accordingly, the physical sensing element is an electrode, a quartz crystal microbalance (QCM), a flexural plate wave (FPW) device, a thermal sensing element, a pressure sensing element, an optical sensing element or a viscosity sensing element. One embodiment of the first and second analyzing elements is quartz crystal microbalance (QCM).

Accordingly, the biological sensing element is a nucleic acid, protein, antibody, enzyme, microorganism or other biochemical substances.

Accordingly, the fluid analyzing apparatus further comprises at least one bolt to combine the first, second and third units.

Accordingly, the dispersing portion of the first unit is circular.

Accordingly, the first, second and third units are composed of acrylic, Teflon or glass.

Accordingly, the fluid analyzing apparatus further comprises a pump to pump the multiplex fluid sample into the fluid analyzing apparatus.

Accordingly, the multiplex fluid sample is respectively analyzed or detected by the each of analyzing elements.

A detailed description is given in the following embodiments with reference to is the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

First Embodiment

Figure 1:
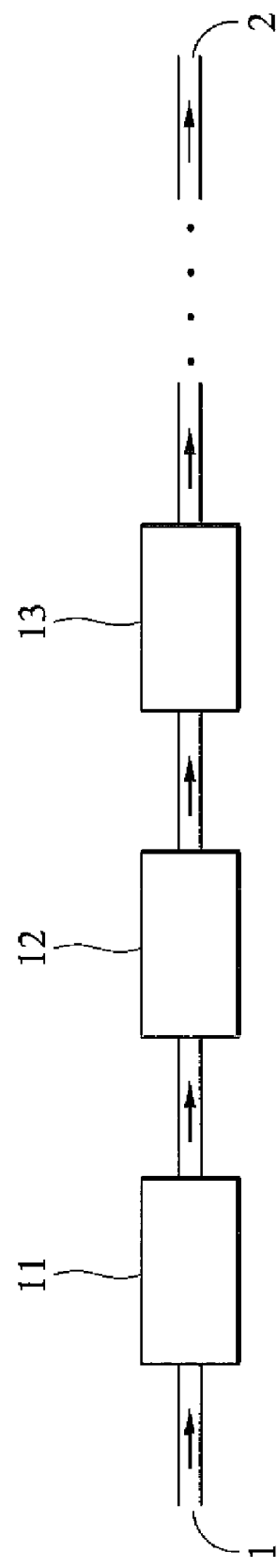
FIG. 1 is a schematic view showing the concept of sequential analysis of the fluid analyzing apparatus of the invention.

Referring to FIG. 1, the fluid analyzing apparatus of this embodiment is directed to the concept of sequential analysis of a multiplex fluid sample. The multiplex fluid sample sequentially flows through a first target chamber 11, a second target chamber 12, a third target chamber 13 and so on via a fluid inlet 1. Then, the multiplex fluid sample flows out via a fluid outlet 2. Additionally, same or different analyzing elements are respectively disposed in the first target chamber 11, second target chamber 12 and third target chamber 13 to analyze the multiplex fluid sample or sieve out specific constituents from the multiplex fluid sample.

Figure 2A:
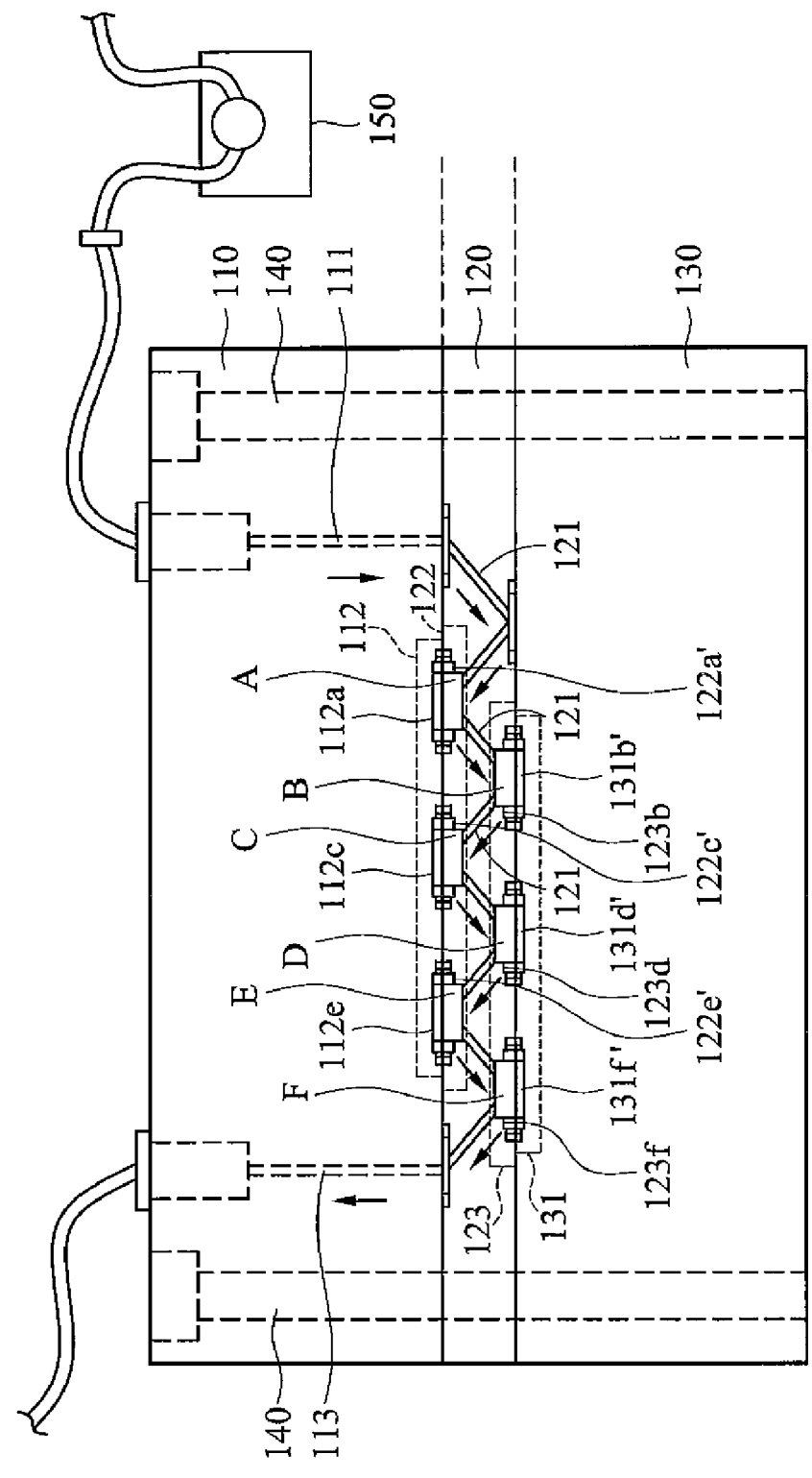
FIG. 2A shows the inner structure of the fluid analyzing apparatus of the first embodiment of the invention.

Referring to FIG. 2A, the fluid analyzing apparatus 100 includes a first unit 110, a second unit 120 and a third unit 130. The first unit 110 has a fluid inlet 111, a first upper analyzing elements fixation portion 112 that includes a first upper fixation space of analyzing element 112a, a third upper fixation space of analyzing element 112c, a fifth upper fixation space of analyzing element 112e, and a fluid outlet 113. Meanwhile, the first upper analyzing elements fixation portion 112 is formed on the lower part of the first unit 110 and is correspond to the first lower analyzing elements fixation portion 122 of the second unit 120.

The second unit 120 is disposed under the first unit 110 and has a fluid transmission pipeline 121, a first lower analyzing elements fixation portion 122 that includes a first lower fixation space of analyzing element 122a', a third lower fixation space of analyzing element 122c', a fifth lower fixation space of analyzing element 122e', and a second upper analyzing elements fixation portion 123 that includes a second upper fixation space of analyzing element 123b, a fourth upper fixation space of analyzing element 123d, a sixth upper fixation space of analyzing element 123f. Meanwhile, the first lower analyzing elements fixation portion 122 is formed on the upper part of the second unit 120 and is correspond to the first upper analyzing elements fixation portion 112 of the first unit 110. The second upper analyzing elements fixation portion 123 is formed on the lower past of the second unit 120 and is correspond to the second lower analyzing elements fixation portion 131 of the third unit 130.

The third unit 130 is disposed under the second unit 120 and has a second lower analyzing elements fixation portion 131 that includes a second lower fixation space of analyzing element 131b', a fourth lower fixation space of analyzing element is 131d', a sixth lower fixation space of analyzing element 131f'. Meanwhile, the second lower analyzing elements fixation portion 131 is formed on the upper pail of the third unit 130 and is correspond to the second upper analyzing elements fixation portion 123 of the second unit 120.

As shown in FIG. 2A, when the first unit 110, second unit 120 and third unit 130 are fixed together by two bolts 140, a first target chamber A, a third target chamber C, and a fifth target chamber E are formed by combination of the first upper analyzing elements fixation portion 112 of the first unit 110, the first lower analyzing elements fixation portion 122 of the second unit 120, and the upper analyzing elements, a second target chamber B, a fourth target chamber D, and a sixth target chamber F are formed by combination of the second upper analyzing elements fixation portion 123 of second unit 120, the second lower analyzing elements fixation portion 131 of the third unit 130, and lower analyzing elements. Meanwhile, the fluid transmission pipeline 121 of the second unit 120 is sequentially connected to the fluid inlet 111 of the first unit 110, first target chamber A, second target chamber B, third target chamber C, fourth target chamber D, fifth target chamber E, sixth target chamber F and fluid outlet 113 of the first unit 110 with an inclined angle of 45 degrees. Thus, the multiplex fluid sample can smoothly flow in the pipeline 121 and bubbles halting therein may be prevented (particularly when the multiplex fluid sample is liquid and the diameter of the pipeline 121 is small, such as 1 mm).

Figure 2B:
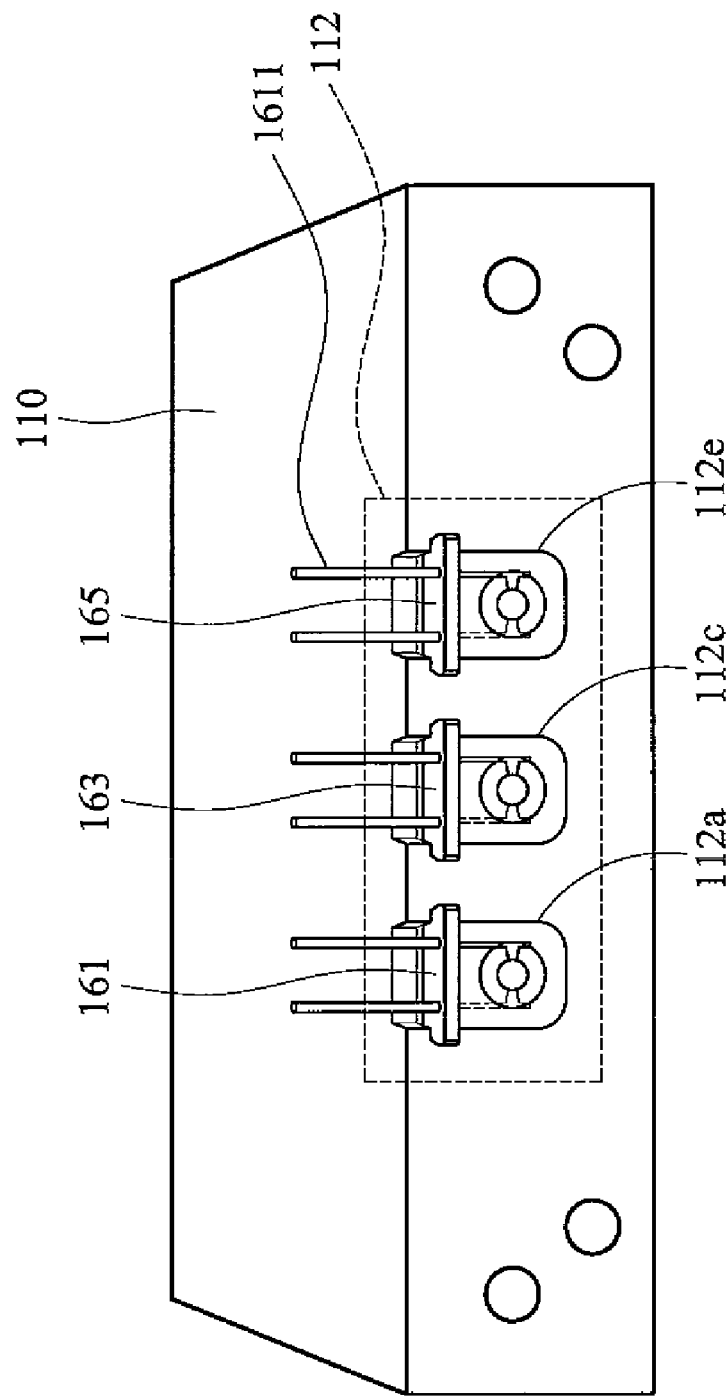
FIG. 2B shows a detailed structure of a first unit of the first embodiment of the invention.
Figure 2C:
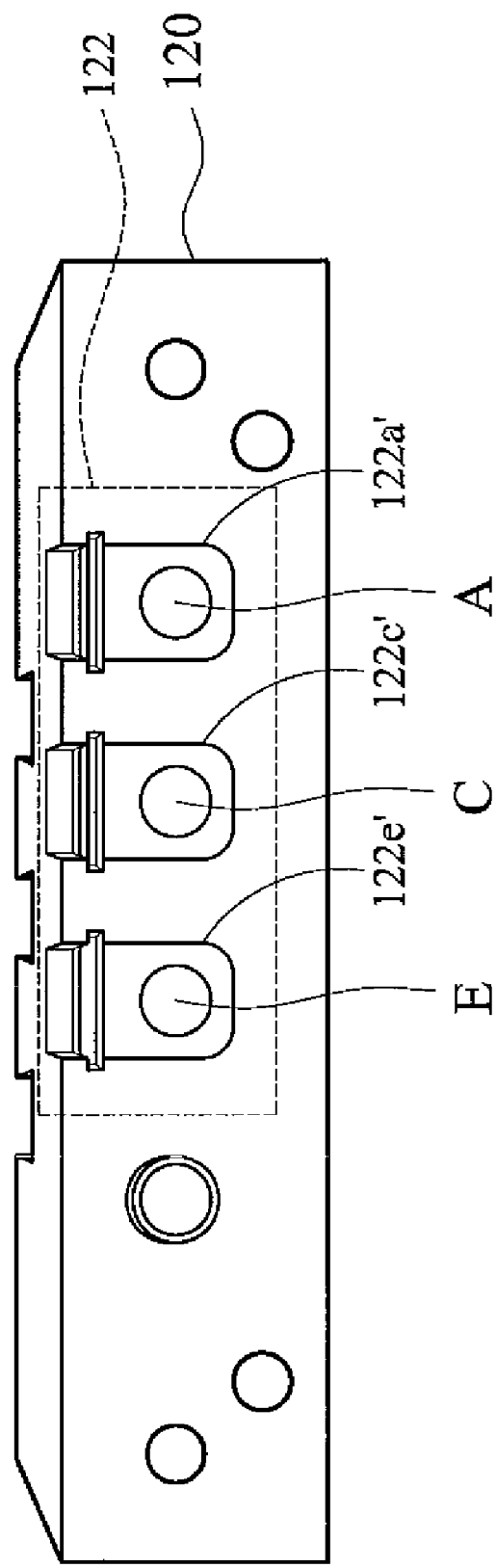
FIG. 2C shows a detailed structure of upper side of a second unit of the first embodiment of the invention.
Figure 2D:
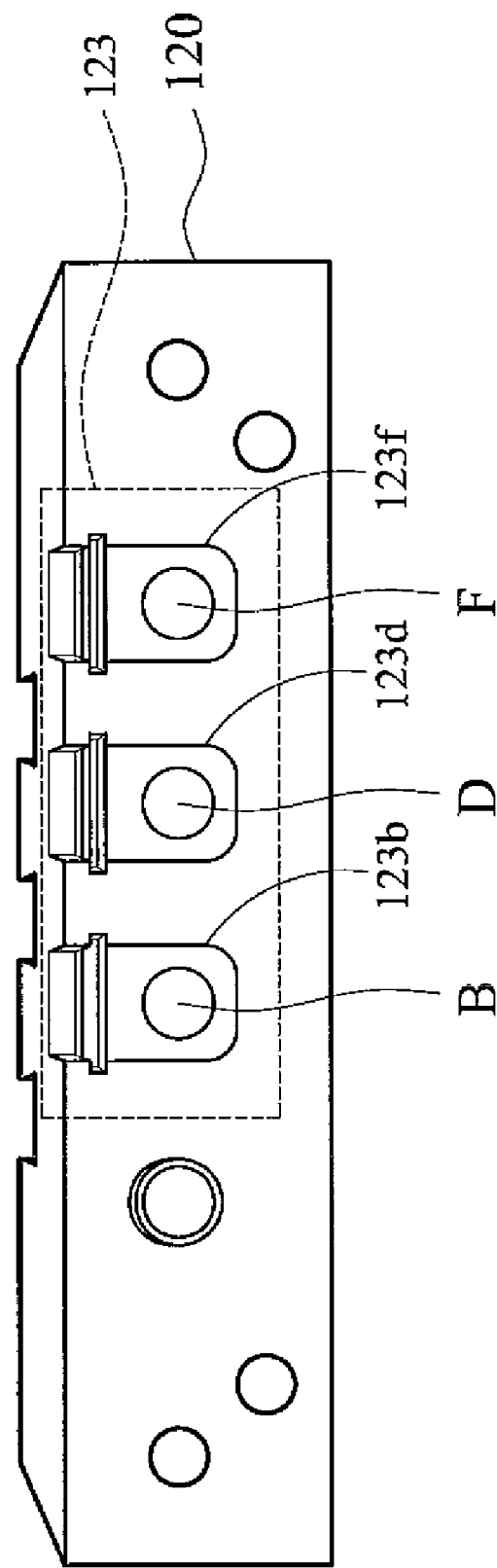
FIG. 2D shows a detailed structure of lower side of a second unit of the first embodiment of the invention.
Figure 2E:
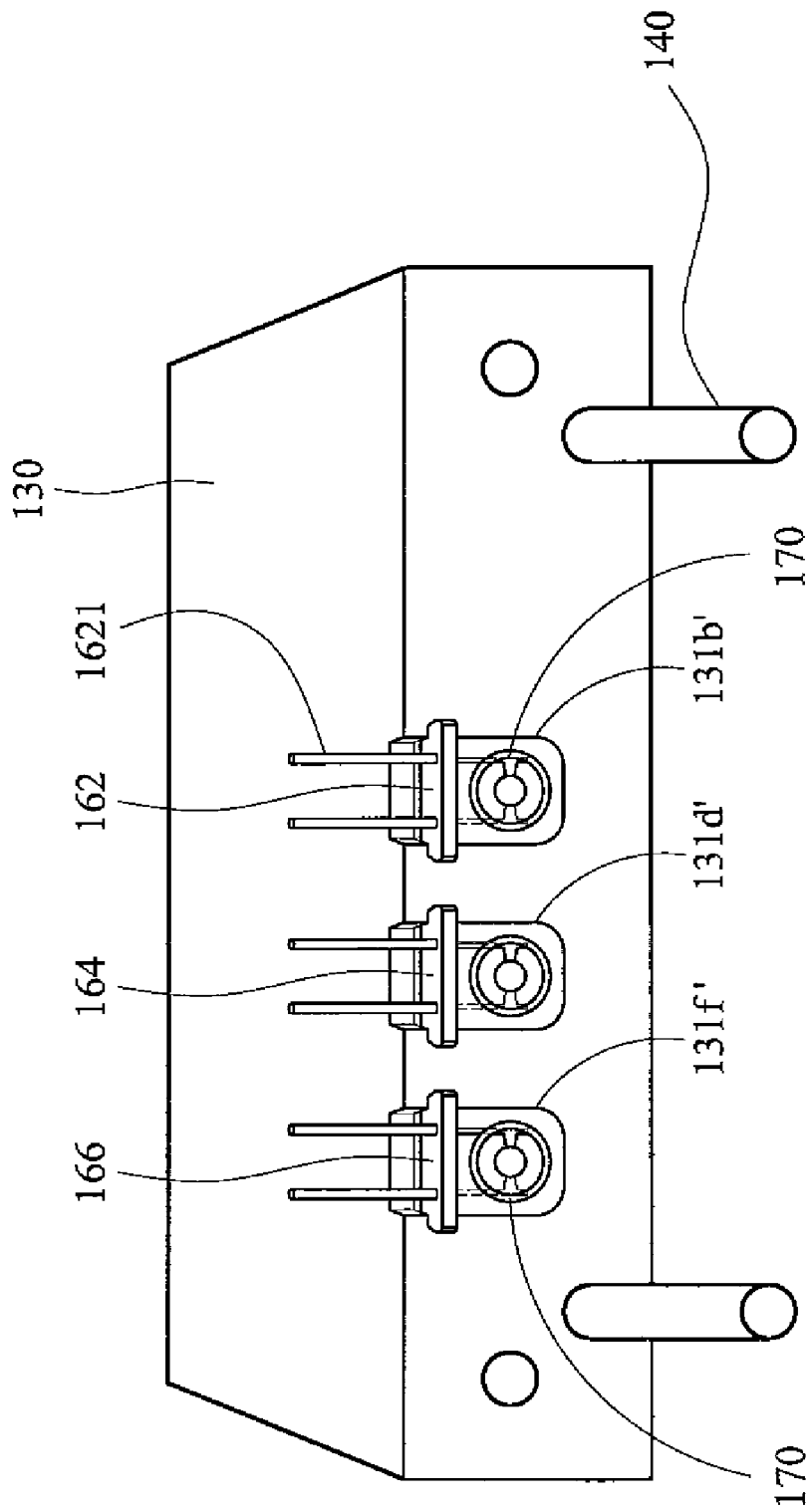
FIG. 2E shows a detailed structure of a third unit of the first embodiment of the invention.

FIG. 2B shows a detailed structure of a first unit of the first embodiment of the invention. FIG. 2C shows a detailed structure of upper side of a second unit of the first embodiment of the invention. FIG. 2D shows a detailed structure of lower side of a second unit of the first embodiment of the invention. FIG. 2E shows a detailed structure of a third unit of the first embodiment of the invention. With reference to FIGS. 2B and 2E, a first analyzing element 161, a second analyzing element 162, a third analyzing element 163, a fourth analyzing element 164, a fifth analyzing element 165, a sixth analyzing element 166 are respectively disposed with O-ring 170 between a first upper fixation space of analyzing element 112a and a first lower fixation space of analyzing element 122a', a second upper fixation space of analyzing element 123b and a second lower fixation space of analyzing element 131b', a third upper fixation space of analyzing element 112c and a third lower fixation space of analyzing element 122c', a fourth upper fixation space of analyzing element 123d and a fourth lower fixation space of analyzing element 131d', a fifth upper fixation space of analyzing element 112e and a fifth lower fixation space of analyzing element 122e' and a sixth upper fixation space of analyzing element 123f and a sixth lower fixation space of analyzing element 131f'. The first analyzing element 161 has first signal connecting portion 1611 extending out of the fluid analyzing apparatus. The second analyzing element 162 has second signal connecting portion 1621 extending out of the fluid analyzing apparatus.

The first, second, third, fourth, fifth and sixth analyzing element may have different analyzing functions. For example, the first, second, third, fourth, fifth and sixth analyzing element may be a physical sensing element, a biological sensing element or a chemical sensing element which requires an additional identification element and a specific transducer. The physical sensing element may be and is not limited to an electrode, a quartz crystal microbalance (QCM), a flexural plate wave (FPW) device, a thermal sensing element, a pressure sensing element, an optical sensing element or a viscosity sensing element. The biological sensing element is a nucleic acid, protein, antibody, enzyme, microorganism or other biochemical substances. Additionally, the first, second, third, fourth, fifth and sixth analyzing element respectively have a first signal connecting portion 1611, a second signal connecting portion 1621, a third signal connecting portion (not shown), a fourth signal connecting portion (not shown), a fifth signal connecting portion (not shown) and a sixth signal connecting portion (not shown) extending out of the fluid analyzing apparatus 100 to output corresponding analyzing signals to other devices for further processing.

Accordingly, since the multiplex fluid sample flows in the fluid transmission pipeline 121, first target chamber A, second target chamber B, third target chamber C, fourth target chamber D, fifth target chamber E and sixth target chamber F, a sealing element, such as a rubber O-ring, is disposed between the upper analyzing elements is fixation portion and lower analyzing elements fixation portion to prevent the multiplex fluid sample from flowing out of each target chamber via the connection thereof.

Specifically, the fluid analyzing apparatus 100 is not limited to the six target chambers A, B, C, D, E and F. Namely, the fluid analyzing apparatus 100 may have more target chambers to analyze and detect the multiplex fluid sample.

The fluid analyzing apparatus 100 of this embodiment has the following advantages. The fluid analyzing apparatus 100 may be manufactured by means of a common mechanical process, thereby reducing the manufacturing costs thereof. The fluid analyzing apparatus 100 can be disassembled to three units, such that the analyzing elements therein are easily disposed and replaced. Each target chamber has a predetermined volume, such that the amount of fluid in each target chamber increases and the reaction sensitivity thereof is enhanced. The fluid analyzing apparatus 100 can analyze and detect a small amount of fluid, particularly when only a small amount of fluid, such as a drop of blood, exists. Since the pipeline 121 is connected to the first, second, third, fourth, fifth and sixth target chambers with an inclined angle (45 degrees), the bubbles formed therein can be easily removed by the sample when the sample is liquid. Thus, interference does not occur during analysis.

Example 1

In preferred embodiment, the fluid analyzing apparatus 100 is composed of acrylic and the size thereof is approximately 90 mm×20 mm×49 mm. The diameter of the pipeline 121 is 1 mm. The volume of each target chamber is equal to or smaller than 30 μL. And QCM was used as analysis elements.

When a multiplex fluid sample, particularly a multiplex fluid sample with mixed substances, is pumped into the fluid analyzing apparatus 100 via the fluid inlet 111 by a pump (peristaltic pump) 150, the multiplex fluid sample flows into the first target chamber A, second target chamber B, third target chamber C, fourth target chamber D, fifth target chamber B and sixth target chamber F in sequence. The analyzing element disposed in each target chamber reacts with specific constituents in the multiplex fluid sample to output a corresponding signal. Then, the multiplex fluid sample flows out of the fluid analyzing apparatus 100 via the fluid outlet 113.

Figure 5:
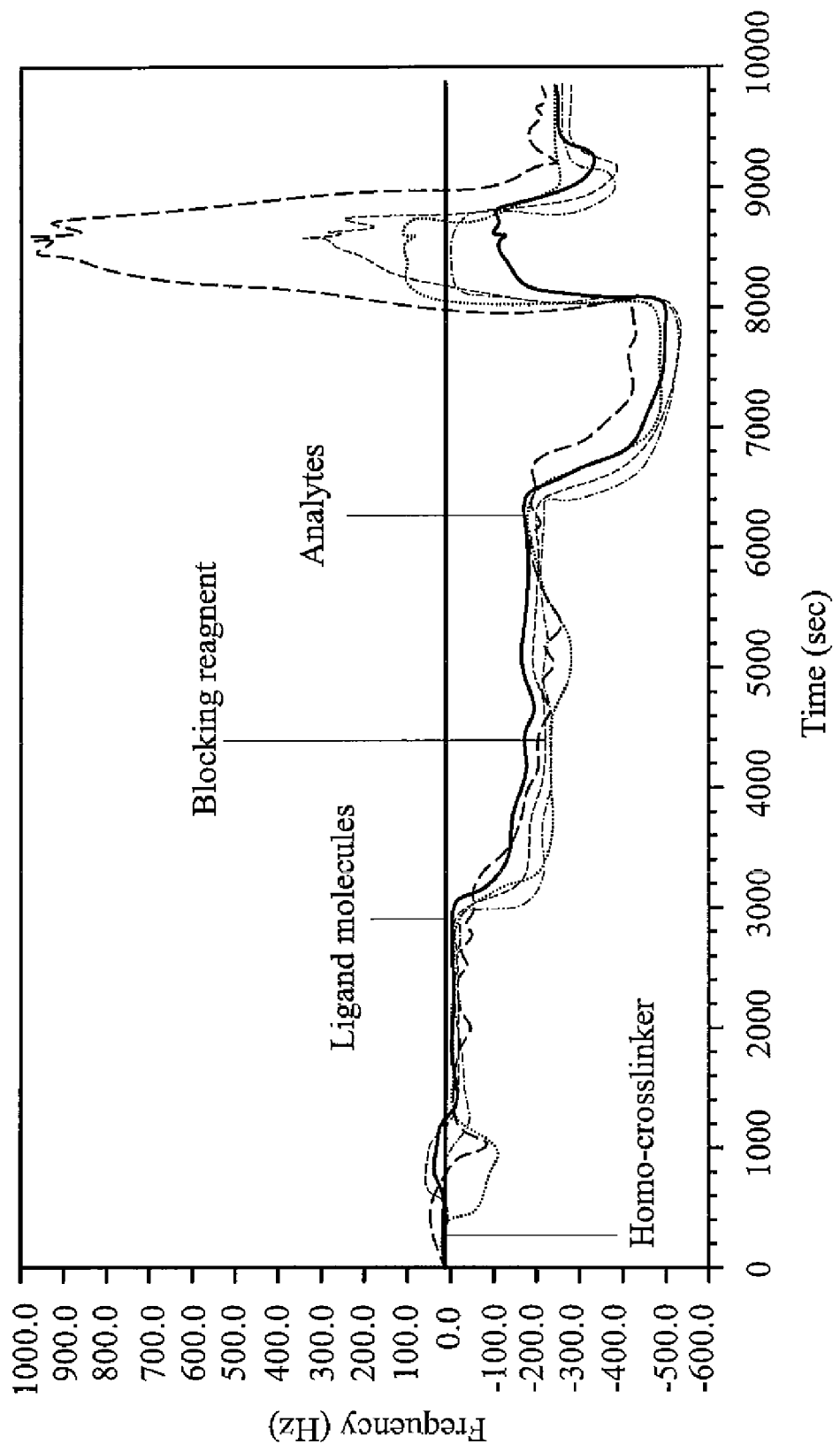
FIG. 5 shows the signal which involved the antibodies immobilization and analyte detection from the use of fluid analyzing apparatus.

FIG. 5 shows the signal which involved the antibodies immobilization and analyte detection from the use of fluid analyzing apparatus 100. The response of each analyzing element could be distinguished clearly through a sequential flow process.

Second Embodiment

Figure 3:
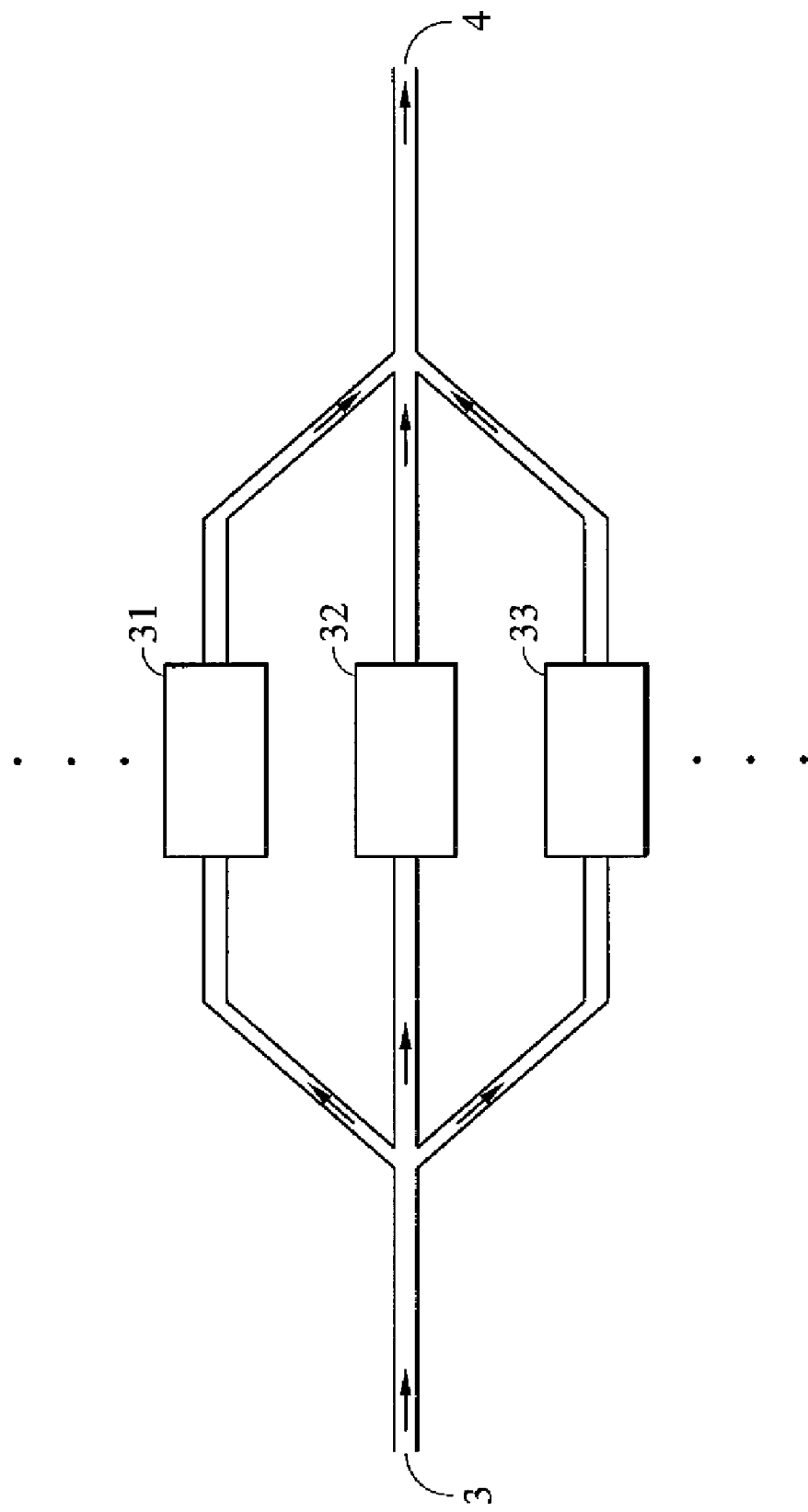
FIG. 3 is a schematic view showing the concept of simultaneous analysis of the fluid analyzing apparatus of the invention.

Referring to FIG. 3, the fluid analyzing apparatus of this embodiment is directed to the concept of simultaneous analysis of a multiplex fluid sample. The multiplex fluid sample simultaneously flows through a first target chamber 31, a second target chamber 32, a third target chamber 33 and so on via a fluid inlet 3. Then, the multiplex fluid sample gathers and flows out via a fluid outlet 4. Additionally, same or different analyzing elements are respectively disposed in the first target chamber 31, second target chamber 32 and third target chamber 33 to analyze the multiplex fluid sample or sieve out specific constituents from the multiplex fluid sample.

Figure 4:
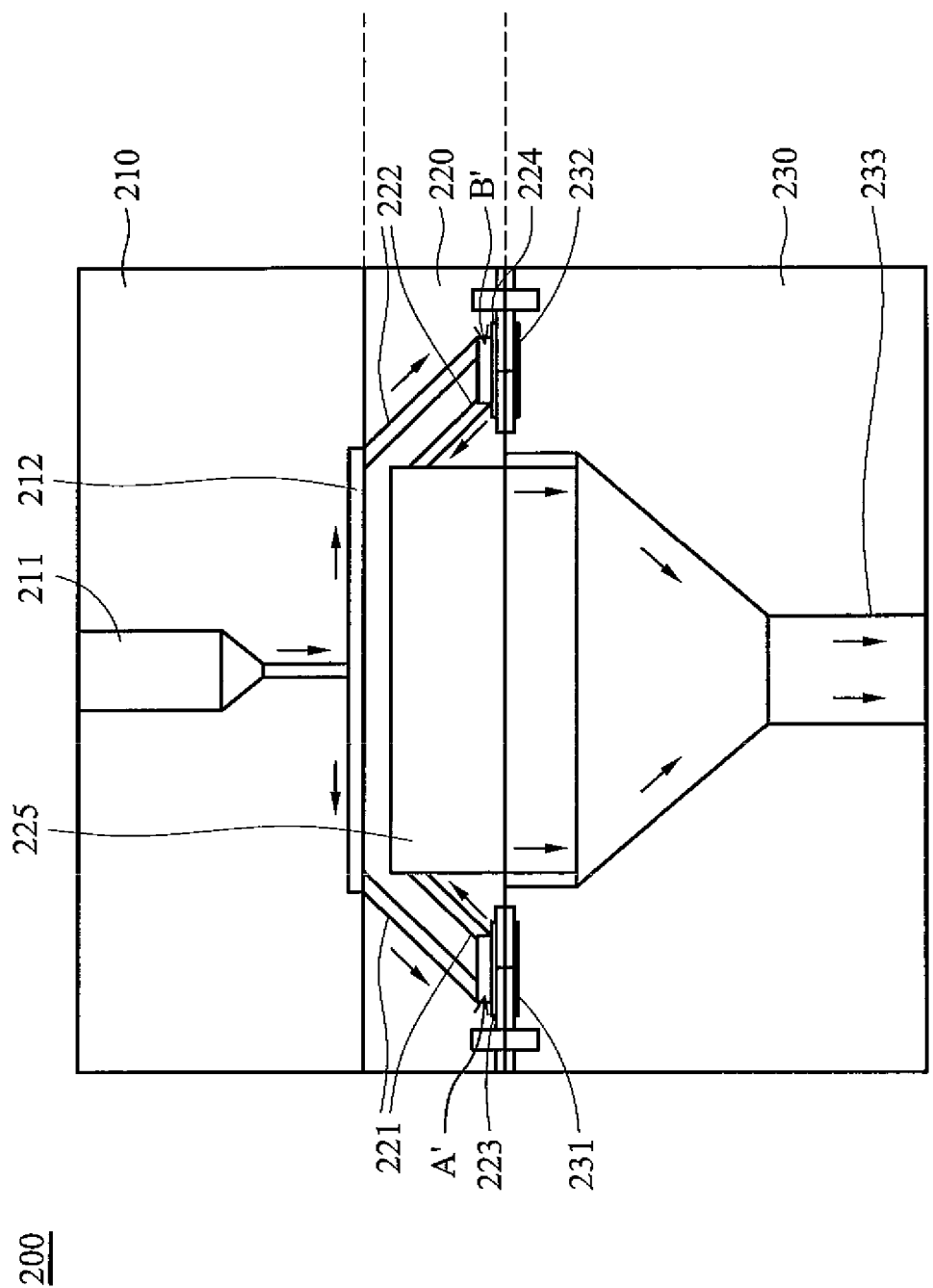
FIG. 4 shows the inner structure of the fluid analyzing apparatus of the second embodiment of the invention.

Referring to FIG. 4, the fluid analyzing apparatus 200 includes a first unit 210, a second unit 220 and a third unit 230. The first unit 210 has a fluid inlet 211 and a dispersing portion 212. Meanwhile, the dispersing portion 212 is formed on the lower past of the first unit 210 and connected to the fluid inlet 211. Additionally, the dispersing portion 212 is circular.

The second unit 220 is disposed under the first unit 210 and has a first pipeline 221, a second pipeline 222, a collective portion 225, the upper analyzing elements fixation portion that includes a first upper fixation space of analyzing element 223 and a second upper fixation space of analyzing element 224. Meanwhile, the upper analyzing elements fixation portion and collective portion 225 are formed on the lower past of the second unit 220.

The third unit 230 is disposed under the second unit 220 and has a fluid outlet 232, the lower analyzing elements fixation portion that includes a first lower fixation space of analyzing element 231 and a second lower fixation space of analyzing element 232. Meanwhile, the lower analyzing elements fixation portion is formed on the upper part of the third unit 230 and corresponds to the upper analyzing elements fixation portion 223 of the second unit 220.

As shown in FIG. 4, when the first unit 210, second unit 220 and third unit 230 are fixed together by a bolt (not shown), a first target chamber A' and a second target chamber B' are formed by the combination of the upper analyzing elements fixation portion, the lower analyzing elements fixation portion and the analyzing elements. Meanwhile, the first pipeline 221 of the second unit 220 is connected to the dispersing portion 212 of the first unit 210, first target chamber A' and collective portion 225 with an inclined angle of 45 degrees, and the second pipeline 222 of the second unit 220 is connected to the dispersing portion 212 of the first unit 210, second target chamber B' and collective portion 225 with the same inclined angle of 45 degrees. Thus, the multiplex fluid sample can flow smoothly in the first pipeline 221 and second pipeline 222 and bubbles halted therein may be prevented, specifically when the sample is liquid and the diameter of the first pipeline 221 and second pipeline 222 is small, such as 1 mm.

Additionally, a first analyzing element (not shown) and a second analyzing element (not shown) are respectively disposed in the first target chamber A' and second target chamber B'. The first and second analyzing elements may have different analyzing functions. For example, the first and second analyzing elements may be a physical sensing element, a biological sensing element or a chemical sensing element which requires an additional identification element and a specific transducer. The physical sensing element may be and is not limited to an electrode, a quartz crystal microbalance (QCM), a flexural plate wave (FPW) device, a thermal sensing element, a pressure sensing element, an optical sensing element or a viscosity sensing element. The biological sensing element is a nucleic acid, protein, antibody, enzyme, microorganism or other biochemical substances. Additionally, the first and second analyzing elements respectively have a first signal connecting portion (not shown) and a second signal connecting portion (not shown) extending out of the fluid analyzing apparatus 200 to output corresponding analyzing signals to other devices for further processing.

Accordingly, since the multiplex fluid sample flows in the first pipeline 221, first target chamber A', second pipeline 222 and second target chamber B', a sealing element, such as a rubber O-ring, is disposed between the upper portion and lower portion of each target chamber to prevent the multiplex fluid sample from flowing out of each target chamber via the connection thereof.

In this embodiment, the fluid analyzing apparatus 200 is composed of acrylic and the size thereof is approximately 60 mm (diameter)×60 mm (height). The diameter of the first pipeline 221 and second pipeline 222 is 1 mm. The volume of each target chamber is equal to or smaller than 30 μL.

When a multiplex fluid sample, particularly a multiplex fluid sample containing a mixture of substances, is pumped into the fluid analyzing apparatus 200 via the fluid inlet 211 by a pump (not shown), the multiplex fluid sample flows into the dispersing portion 212 and is thereby dispersed. Then, the multiplex fluid sample simultaneously flows into the first target chamber A' and second target chamber B' via the first pipeline 221 and second pipeline 222. The analyzing element disposed in each target chamber reacts with specific constituents in the multiplex fluid sample to output a corresponding signal. Eventually, the multiplex fluid sample flows into the collective portion 225 via the first pipeline 221 and second pipeline 222 and flows out of the fluid analyzing apparatus 200 via the fluid outlet 233.

Specifically, the fluid analyzing apparatus 200 is not limited to the two target chambers A' and B'. Namely, the fluid analyzing apparatus 200 may have more target chambers to analyze and detect the multiplex fluid sample, thereby reducing the analyzing time thereof.

The fluid analyzing apparatus 200 of this embodiment has the following advantages. The fluid analyzing apparatus 200 may be manufactured by means of a common mechanical process, thereby reducing the manufacturing costs thereof. The fluid analyzing apparatus 200 can be disassembled to three units, such that the analyzing elements therein are easily disposed and replaced. Each target chamber has a predetermined volume, such that the amount of fluid in each target chamber increases and the reaction sensitivity thereof is enhanced. The fluid analyzing apparatus 200 simultaneously analyzes the multiplex fluid sample when the multiplex fluid sample is sufficient, thereby reducing the time spent in analyzing the multiplex fluid sample. Since the first pipeline 221 and second pipeline 222 are respectively connected to the first target chamber A' and second target chamber B' with an inclined angle (45 degrees), the bubbles formed therein can be easily removed by the sample when the sample is liquid. Thus, interference does not occur during analysis.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An fluid analyzing apparatus for sequentially analyzing a multiplex fluid sample, comprising:
    a first unit having a fluid inlet, a fluid outlet, and a first upper analyzing elements fixation portion, wherein the first upper analyzing elements fixation portion is formed on the lower part of the first unit and corresponds to a first lower analyzing elements fixation portion of a second unit;
    the second unit disposed under the first unit and having a fluid transmission pipeline, a first lower analyzing elements fixation portion and a second upper analyzing elements fixation portion, wherein the first lower analyzing elements fixation portion is formed on the upper part of the second unit and corresponds to the first upper analyzing elements fixation portion of the first unit, the second upper analyzing elements fixation portion is formed on the lower part of the second unit and corresponds to a second lower analyzing elements fixation portion of a third unit; and
    the third unit disposed under the second unit and having a second lower analyzing elements fixation portion, wherein second lower analyzing elements fixation portion is formed on the upper part of the third unit and corresponds to the second upper analyzing elements fixation portion of the second unit,
    wherein an upper target chambers are formed on upper part of second unit by combination of the first upper analyzing elements fixation portion, the first lower analyzing elements fixation portion and an analyzing elements,
    wherein an lower target chambers are formed on lower part of second unit by combination of the second upper analyzing elements fixation portion, the second lower analyzing elements fixation portion and the analyzing elements,
    wherein the transmission pipelines of the second unit are sequentially connect the distal portion of pipeline with fluid inlet, first lower analyzing elements fixation portion, second upper analyzing elements fixation portion and distal portion of pipeline with fluid outlet by an inclined angle, wherein the fluid sample flow through sequentially each surface of analyzing elements via fluid inlet, the upper target chambers, the lower target chambers, and fluid outlet, further the multiplex analytes could be determined or detected by analyzing elements, and
    wherein at least one bolt to combine the first, second and third units, further the analyzing elements could be replaced by disassembly and assembly between first, second and third units.

2. The fluid analyzing apparatus as claimed in claim 1, wherein the analyzing elements further comprises a signal connecting portion extending out of the fluid analyzing apparatus.

3. The fluid analyzing apparatus as claimed in claim 1, wherein the analyzing elements are physical sensing elements.

4. The fluid analyzing apparatus as claimed in claim 3, wherein the physical sensing element is a quartz crystal microbalance (QCM).

5. The fluid analyzing apparatus as claimed in claim 1, wherein the analyzing elements are composed of the same or different type of sensing elements.

6. The fluid analyzing apparatus as claimed in claim 1, wherein the first, second and third units are composed of acrylic, Teflon or glass.

7. The fluid analyzing apparatus as claimed in claim 1, further comprising a pump to pump the multiplex fluid sample into the fluid analyzing apparatus.

8. The fluid analyzing apparatus as claimed in claim 1, wherein the analyzing elements are biological or/and chemical sensing elements.

9. The fluid analyzing apparatus as claimed in claim 3, wherein the physical sensing element is an electrode, a flexural plate wave (FPW) device, a thermal sensing element, a pressure sensing element, an optical sensing element or a viscosity sensing element.

10. The fluid analyzing apparatus as claimed in claim 8, wherein the biological sensing element is a nucleic acid, protein, antibody, enzyme, microorganism or other biochemical substances.

* * * * *

UNITED STATES PATENT AND TRADEMARK OFFICE
CERTIFICATE OF CORRECTION

| | |
|---|---|
| PATENT NO. | : 8,216,826 B2 |
| APPLICATION NO. | : 12/251274 |
| DATED | : July 10, 2012 |
| INVENTOR(S) | : Kun-Feng Lee et al. |

It is certified that error appears in the above-identified patent and that said Letters Patent is hereby corrected as shown below:

ON THE TITLE PAGE:

At item (30), correct the Foreign Application Priority Data to read as follows:

--Jan. 21, 2003   (TW)   ............................ 92101221 A--.

Signed and Sealed this
Twenty-eighth Day of May, 2013

Teresa Stanek Rea
*Acting Director of the United States Patent and Trademark Office*